United States Patent [19]

Gottsleben

[11] Patent Number: 5,186,624
[45] Date of Patent: Feb. 16, 1993

[54] DENTAL MEASURING INSTRUMENT AND METHOD

[75] Inventor: Bradley D. Gottsleben, Lincoln, Nebr.

[73] Assignee: Tresco, Inc., Lincoln, Nebr.

[21] Appl. No.: 789,068

[22] Filed: Nov. 7, 1991

[51] Int. Cl.⁵ ............................................. A61C 19/04
[52] U.S. Cl. ....................................................... 433/69
[58] Field of Search ................. 433/68, 69, 72; 33/513

[56] References Cited

U.S. PATENT DOCUMENTS

| | | | |
|---|---|---|---|
| 2,389,063 | 11/1945 | Lang | 433/69 |
| 2,481,203 | 9/1949 | Davies et al. | 433/69 |
| 2,994,957 | 8/1961 | McLeod | 433/69 |
| 3,468,027 | 9/1969 | Dobranski et al. | 433/68 |

Primary Examiner—John J. Wilson
Attorney, Agent, or Firm—Vincent L. Carney

[57] ABSTRACT

To make Gothic tracings, a Gothic scribe comprising a movable member adapted to be mounted by a universal joint to wing members in a plurality of different angles with respect to the wing members and a scribe vertically adjustable with respect to and mounted to the movable member are adjusted with the wing members, and the movable member is locked in the same plane to measure the vertical opening by moving the scribe up to a striking plate and then used to measure the centric relationship. After proper adjustment, another measurement is made with the base plates in place and the movable member unlocked to permit movement. The base plates are locked in place after the jaws have been relaxed with the point of the scribe in the centric relationship and used to make the denture.

5 Claims, 4 Drawing Sheets

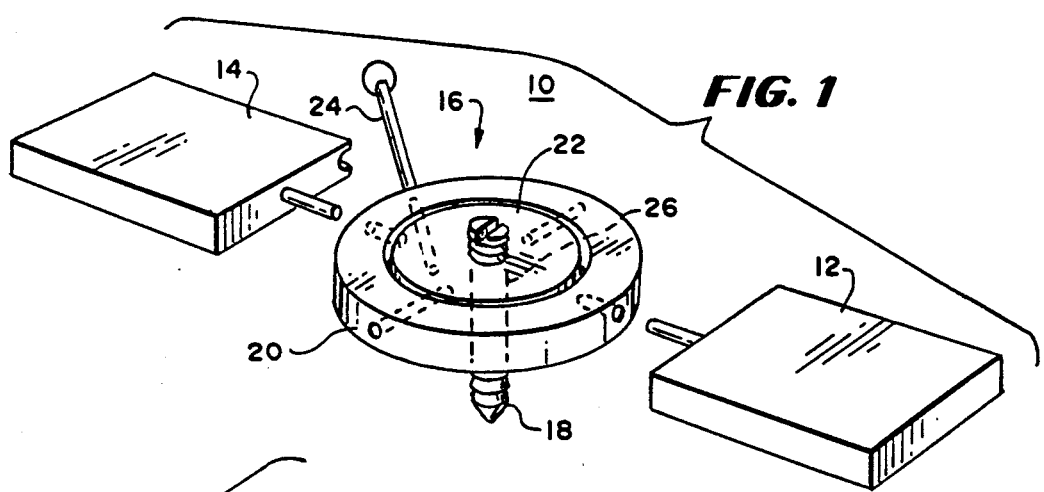
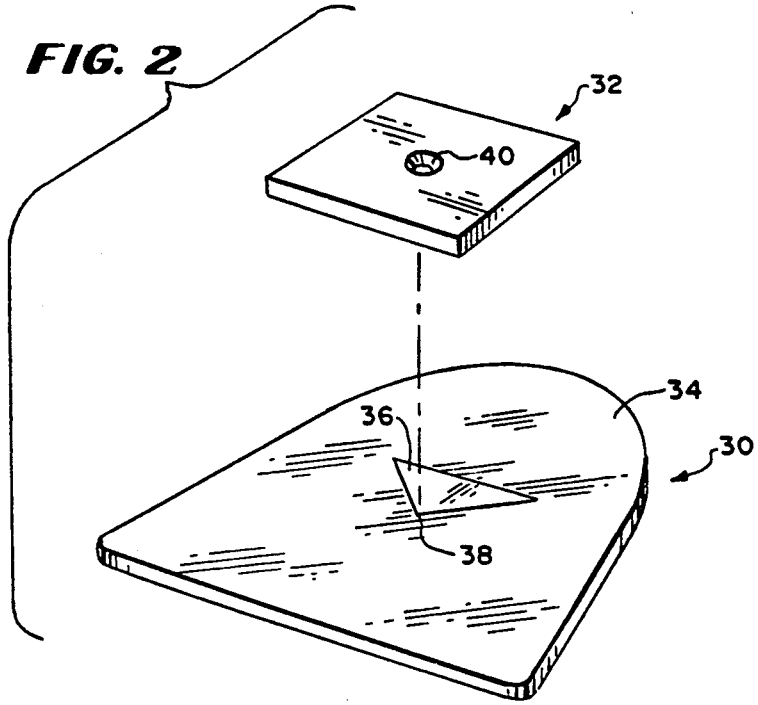
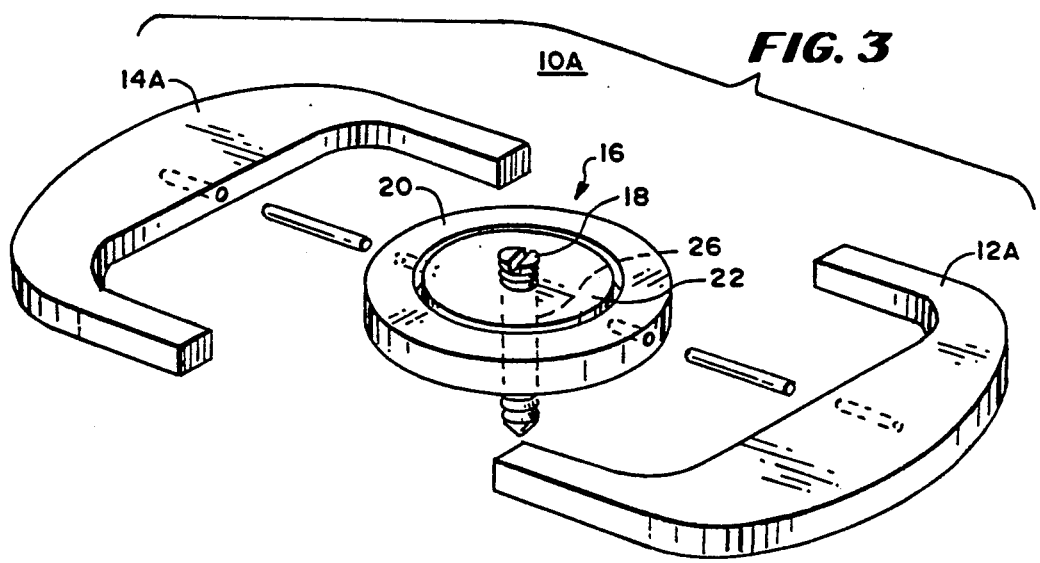

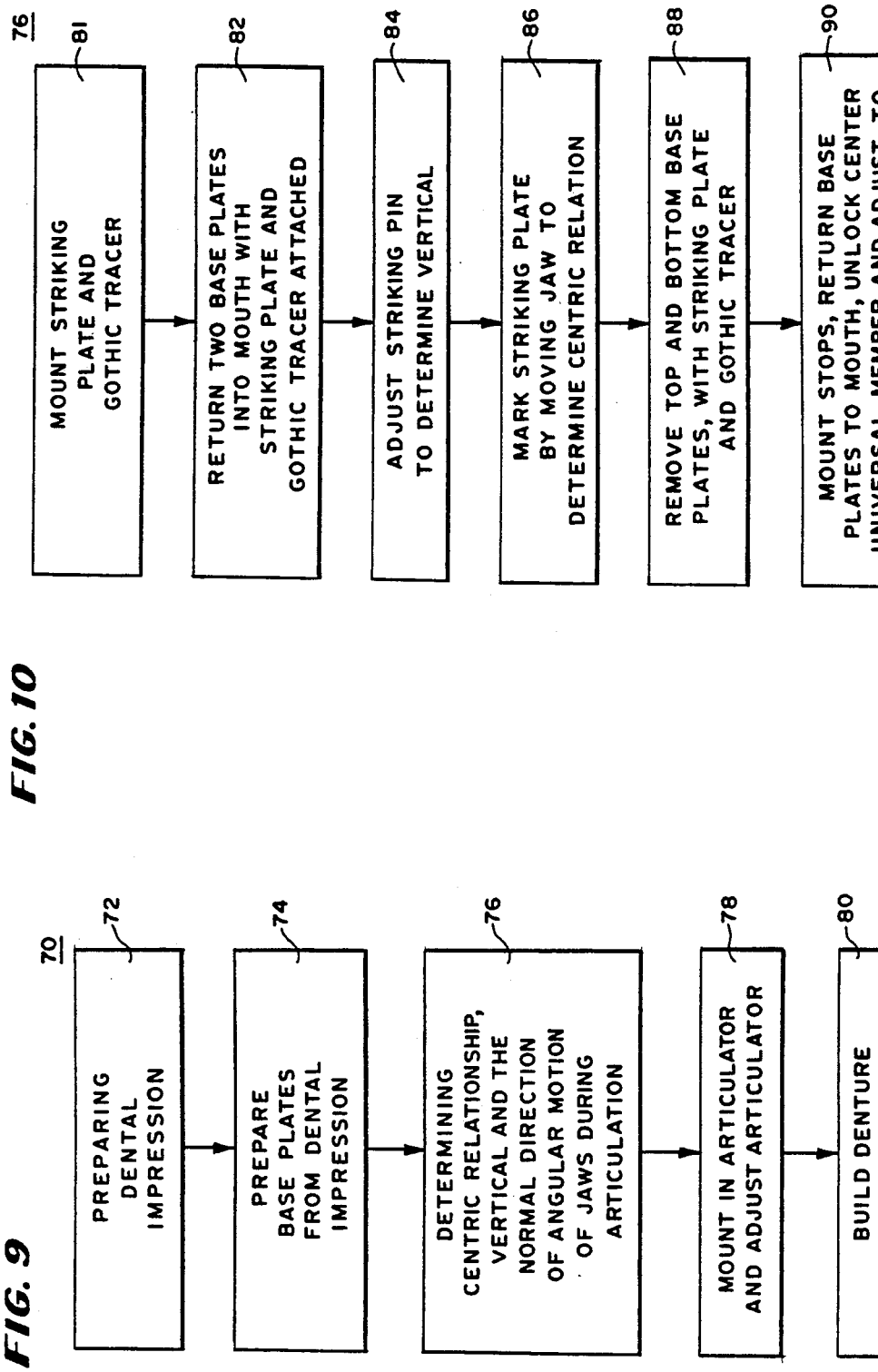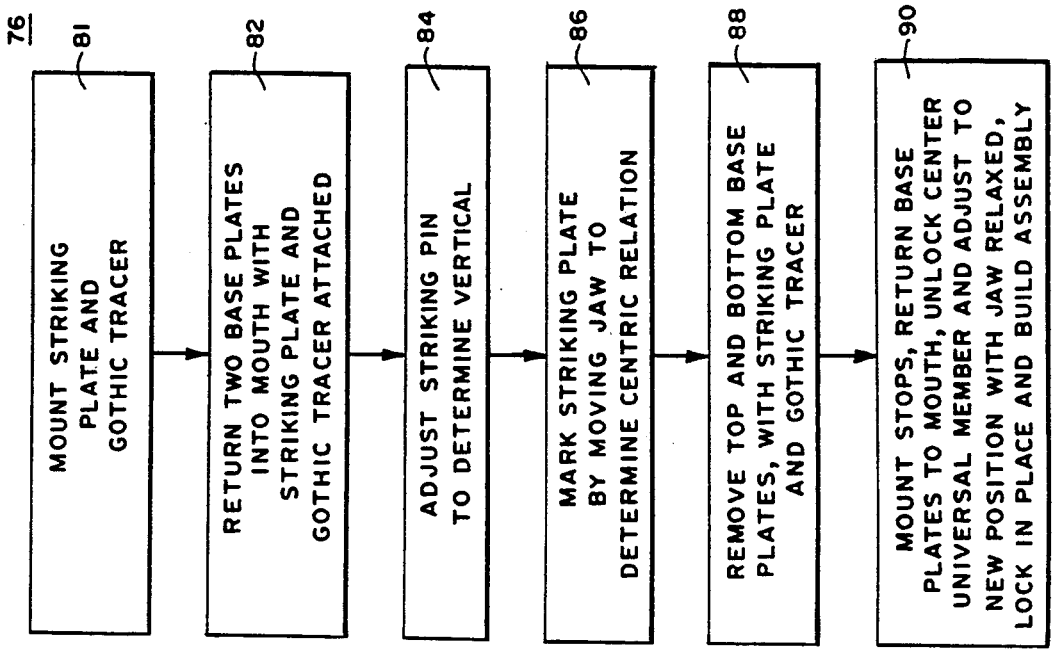

DENTAL MEASURING INSTRUMENT AND METHOD

BACKGROUND OF THE INVENTION

This invention relates to dental measurements as used in dental practice, apparatuses for making the dental measurements and techniques for making them.

Two types of dental measurements are Gothic tracings and vertical openings. They are made in the mouth of a patient using special tools. One such special tool is called a Gothic tracer.

As part of the processes of making Gothic tracings and measuring vertical openings, a dental impression is taken of the patient's mouth and then removed from the patient's mouth. The dental impression encompasses all of the natural landmarks within the mouth including the ridges, palate, buckle, lingual, libual, the teeth, and any other features.

These dental impressions are utilized by the dental technician or by the dentist to make upper and lower base plates. The lower base plate covers those portions of the ridge in which there are no teeth and a substantial portion of the lingual. The upper base plate covers the palate and the portion of the upper ridge in which there are no teeth.

The dentist or the dental technician mounts the base plates and the Gothic tracer together in wax. The Gothic tracer includes an upper portion called a striking plate and a lower portion having a mounting plate and a scribe, which are used in making the dental measurements in cooperation with the striking plate. The scribe includes a vertically adjustable screw member that can be adjusted in the scribe mounting plate to the proper vertical opening of the mouth and used to form triangular scratchings in a coat on the striking plate.

To make the Gothic tracing, the surface of the striking plate is coated on the side facing the scibe before mounting the striking plate and after the Gothic tracer has been mounted in the base plates, the base plates are returned into the mouth of the patient. The patient then moves his mouth in all directions with the tip of the scribe in contact with the striking plate. This action forms scratches in the coat in the form of a triangle and the inner most apex of these substantially triangular scratchings is called the centric relation.

In one prior art Gothic tracer, called the Swissident (trademark of Swissident Corporation) described in U.S. Pat. No. 3,068,570, the center screw or scribe is mounted for only perpendicular motion with respect to an integrally formed mounting plate in the lower portion of the tracer.

The prior art Gothic tracers have several disadvantages, such as: (1) they do not measure the angles of the planes of the jaw necessary for dentist to prepare the denture; and (2) they are limited in some respects in that they are not useful in determining the centric relation for orthodontic devices used for maladies such as dental malocclusion, or the like.

SUMMARY OF THE INVENTION

Accordingly, it is an object of the invention to provide a novel Gothic tracing instrument;

It is a still further object of the invention to provide a novel technique useful in making dentures or other orthodontic appliances such as a bruxism splint used for malocclusion;

It is a still further object of the invention to provide a novel Gothic tracing instrument which is capable of making useful measurements other than those of the centric relationship and vertical opening;

It is a still further object of the invention to make dental measurements that take into account the proper angles of the planes of the mouth when making a proper bite;

It is a still further object of the invention to provide a novel Gothic tracing device and method of making measurements of the centric relationship in a more natural plane of occlusion.

In accordance with the above and further objects of the invention, a novel Gothic tracer includes a mounting plate having a scribe that is both vertically adjustable and angularly adjustable with respect to its mounting plate. In the preferred embodiment, it is located at a substantially central relationship with respect to the mounting plate and mounted with a universal joint that can be locked in at least one position.

Preferably, the mounting plate has an angularly adjustable center plate such as a disc mounted by a gimbal for universal motion with the scribe being perpendicular to the disc and adjustable perpendicularly with respect to the disc.

Two different types of mounting plates are normally available and each of the two types may be of any of a plurality of different sizes. A first type of mounting plate is designed to be mounted to the ridge and is used for patients not having existing teeth that interfere with its use. The second type of mounting plate is designed to be positioned on the lingual and is used for patients having teeth that interfere with the use of the first type.

Preferably, the bottom portion of the Gothic tracer includes two wings, the universal joint and the center disc that holds the scribe. The center disc and universal joint are formed together and the same universal joint and center disc may be attached to the wings of either type of mounting plate and to any size of mounting plate so that sets of mounting plates may include one universal joint, center disc and scribe and a plurality of different wings to form either of the two types of mounting plates and different sizes of mounting plates with only one center disc, scribe and universal joint and a plurality of pairs of wings.

To permit replacement of the wings on the same universal joint and center disc, pin connections are used to connect the wings to the universal joint. Thus, the different types and sizes of wings are replaceably mounted in the preferred embodiment to the center disc by pins about which they can rotate unless locked in place. A locking mechanism is provided to lock the wings and center disc in place.

Preferably, the center disc can be adjusted to different angles within two planes at angles to each other and orthogonal to the plane of the central disc. These adjustments are provided by an outer ring member capable of swiveling on the wing supports with respect to one axis and a center disc which can be swiveled about an axis perpendicular to the one axis mounted in the outer member. The scribe is adjustable at an orthogonal angle to the center disc such as by the reading or other adjustment.

In use, after the base plates have been formed from the dental impression, a Gothic tracer is positioned with wings, universal joint, scribe, striking plate and center disc in p ace. At this time, generally but not necessarily, the center disc lies in substantially the same plane as the two wings and the scribe is perpendicular to that plane.

The striking plate is then mounted to the top of the upper base plate in position so that the scribe engages it when the jaws are moved together. The striking plate at this time has, upon the surface facing the point of the scribe, a coat which may be scratched to expose a color different from the coat in a conventional manner.

The combination base plates and Gothic tracer are then positioned in the mouth of the patient, the vertical opening determined by moving the scribe with respect to the center disc with the center disc locked in the plane of the wings and base, the centric relationship determined by scratching the striking plate, the center disc unlocked so that it can be adjusted in angle, the proper angles determined from the angle of the scribe or center member with the jaw relaxed and, from this information, dentures are prepared which take into account some correction for proper occlusion. Preferably, the locking and unlocking of the center disc with respect to the wings are accomplished by a pin and groove or sleeve lock.

With this arrangement, the vertical opening of the mouth is determined while the scribe is perpendicular to the surface of the entire member by adjusting its height under circumstances that resist accidental change of its height. In the preferred embodiment, the scribe is externally threaded and adjusted in position by turning it within a taped hole in the center disc. The resistance of the screw threads maintain the scribe in the position to which it is adjusted.

While the scribe is adjusted to the vertical opening and is perpendicular to the surface of the scribe, the centric relationship is determined by moving the jaw with the point of the scribe in contact with the coat on the striking plate. The motion of the scribe point on the coat of the striking plate scratches a triangle in the coat on the striking plate. The apex of the triangle is the centric relationship.

After the centric relationship is determined, the assembly is removed from the mouth, a stop member is positioned over the centric relationship to enable the screw point to be relatively fixed at the centric relationship. The stop member may be a plate having an opening in it sized to receive and hold the point of the scribe while permitting the scribe to pivot.

To accommodate different size vertical openings of different patients, different stop members may be provided, each having a different thickness to permit adjustment to the height of the scribe for different heights of vertical openings of the patient's mouths. With this adjustment, the scribe can achieve different angles without coming free of the opening in the stop member for very large vertical openings or very short vertical openings and for small angular displacements of the jaws or large angular displacements of the jaws.

Of course other means may be provided to accommodate the variety of different mouths such as by using different diameter or different shaped pins or different types of stops to accommodate different vertical openings. However, in the preferred embodiment, a choice of a limited number of different thicknesses of stop members, each having an opening to overlie the centric relationship, with each stop member being held in place by wax or other adhesive solves this problem.

With the stop member in place, the assembly is returned to the patient's mouth with the center disc and both inner and outer rings unlocked so that the patient's jaw can assume a relaxed, natural position. At this time, the pin may achieve an angle. It is locked at this angle such as by surrounding it with a hardenable material before removing the assembly. The assembly is now removed from the patient's mouth and utilized to make the denture.

It is now possible for the dentist or dental technician to remount the assembly to the original dental impressions, fasten them together and mount to an articulator. It can then be properly positioned in an articulator and the assembly removed to permit the proper molding of the dentures.

From the above description, it can be understood that the Gothic tracer and technique of this invention has several advantages, such as: (1) it permits the dentures to be originally manufactured in a manner that better takes occlusion of the patient into account; (2) it permits easy adjustment by the dentist during the making of measurements by the Gothic tracer to account for the angle of the jaw when the patient's jaws are relaxed; (3) it permits the use of the same instrument utilized as a Gothic tracer to prepare certain types of splints or other orthodontic devices; (4) it permits the preparation of dentures with a smaller amount of chair time and irritation of the patient; and (5) it is relatively economical and easy to use.

SUMMARY OF THE DRAWINGS

The above noted and other features of the invention will be better understood from the following detailed description when considered with reference to the accompanying drawings, in which:

FIG. 1 is an exploded perspective view of a lower portion of a Gothic tracer having a center universal mounting member and scribe;

FIG. 2 is an exploded perspective view of an upper portion of a Gothic tracer having a striking plate and stop member for cooperating with the lower portion of the Gothic tracer of FIG. 1;

FIG. 3 is an exploded perspective view of the lower portion of another embodiment of Gothic tracer;

FIG. 9 is a block diagram of a technique for making dental appliances in which the embodiments of FIGS. 1-8 may be useful; and FIG. 10 is a block diagram of a portion of the process of FIG. 9.

DETAILED DESCRIPTION

Figure 4:
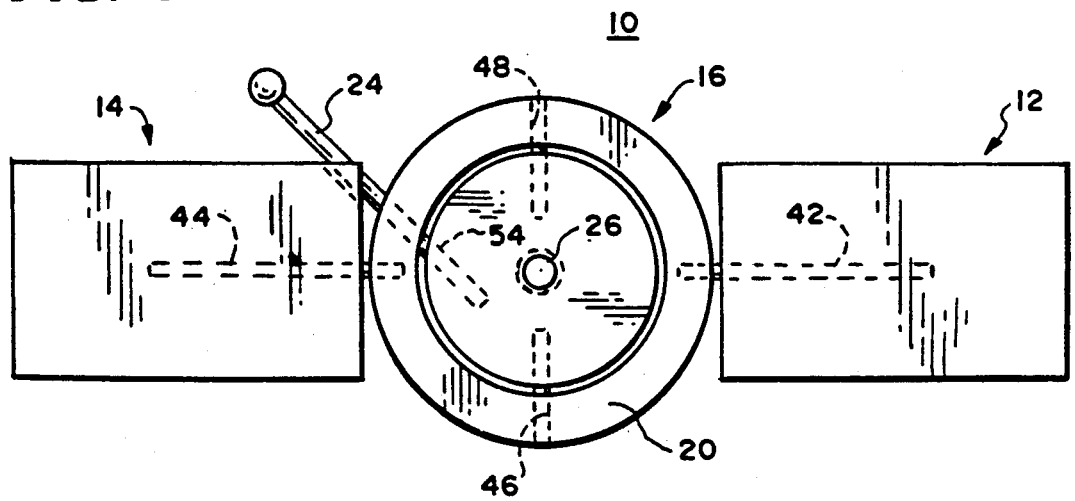
FIG. 4 is a plan view of the lower portion of the Gothic tracer of FIG. 1.

In FIG. 1, there is shown an exploded, perspective view, viewed from the bottom, of the lower portion 10 of a Gothic tracer having a right wing 12, a left wing 14, a central universal member 16, and a scribe 18. The scribe 18 is threaded through a tapped hole 26 in the center of the central universal member 16 for adjustment in a direction perpendicular to the central universal member 16 and for articulation about two perpendicular axes to any angle, with the central universal member 16 being mounted rotatably to the right and left wings 12 and 14.

In this embodiment, the right and left wings 12 and 14 are right regular parallepipeds that when attached to the center universal member 16 may form a bar which can be positioned across the arc of the ridge of an upper or lower base plate formed from a patient's mouth, unless teeth interfere with such placement. With this arrangement, the central universal member 16 can be locked in a single plane with the right or left members positioned across the ridge for measurement of the vertical opening by elevation or retraction of the scribe and for location of the centric relationship in cooperation with a striking plate in a manner to be described hereinafter.

To permit universal motion of the scribe 18, the central universal member 16 includes a center disc 22 and a universal joint. The universal joint includes an outer annular ring 20 having in its center the center disc 22 with a tapped hole 26 in its center to receive the externally threaded scribe 18. The outer ring 20 is fastened by a rotatable joint to the right and left wings 12 and 14 for rotation with respect thereto and to the center disc 22 for rotation about an axis perpendicular to the axis of rotation with respect to the wings to provide a universal joint that permits the scribe 18 to be positioned at any angle with respect to the plane of the wings 12 and 14.

To mount the center disc 22 for rotation, the center disc 22 has at circumferentially opposite locations diametrically aligned with each other two inwardly radially extending holes which are alignable with similar radially extending holes from the center portion of the outer ring 20 so that the center disc 22 may be mounted by pins to the outer ring 20 for rotation with respect to the outer ring 20 about the pins. Two holes in the outer ring 20, 45 degrees removed from the holes that provide rotationable motion between the center disc 22 and the outer ring 20, receive pins that pass through the wings 12 and 14 to provide rotation about an axis perpendicular to the axis of rotation of the center disc 22 with respect to the outer ring 20.

To permit locking of the center disc 22, outer ring 20 and wings 12 and 14 with their top surfaces in the same plane and their bottom surfaces in another parallel plane, a locking pin 24 passes through a portion of one of the wings 12, the outer ring 20 and the center disc 22 to lock the universal joint, center disc and at least one of the wings in the same plane.

In FIG. 2 there is shown an exploded perspective view of a striking plate 30 and a stop member 32 forming the upper portion of a Gothic tracer. The striking plate 30 is a flat member, usually made of aluminum or plastic, having top and bottom wide surfaces, being relatively thin and at times having a removable coat 34 applied to one surface. This coat 34 is scratched by the scribe 18 (FIG. 1) in one of the steps for making a denture to scratch out a substantially triangular area 36 having an apex 38 called the centric relationship.

The stop member 32 is a thin, flat member generally shaped as a right regular parallopiped having an aperture 40 at one location. It is adapted to be fastened with the aperture 40 overlying the centric relationship 38 in one step of the process for making dentures in a manner to be described hereinafter.

Several different stop members 32 are usually available, with each having a different thickness adapted to compensate for different vertical openings although this compensation may be made by using striking plates 30 of different thicknesses rather than changing the thickness of the stop member 32 or by using different striking pins 18 or by other similar measures to accommodate more directly the point of the scribe 18 in the aperture 40 during a certain step in the process of making a denture to be explained hereinafter.

Generally speaking, the length from the distal end of the wing plate 12 to the wing plate 14 in FIG. 1 should be less than 75 millimeters but more than 25 millimeters and in the preferred embodiment is approximately 50 millimeters although different sizes may be used to accommodate different arcs of ridges. The changes in the length are generally reflected in changes in the length of the two wings 12 and 14 rather than the center disc 22 or the universal joint, with the length of a medium wing being approximately 15 millimeters and a smaller wing 10 millimeters. In the preferred embodiment, the outer ring 20, (FIG. 1) will generally have a diameter of 18 millimeters and the center disc 22 and outer diameter of 12 millimeters.

To permit rotation of the striking pin 18 to different angles, the apertures in he universal joint for receiving the pins between the center disc 22 and outer ring 20 and the outer ring 20 and the right and left wings 12 and 14 generally have an outer diameter of about five millimeters which is similar to the outer diameter of the pins that fit therein. A similar diameter is provided to the locking pin and they generally have lengths of approximately a centimeter although these dimensions are not critical and it is only necessary for the pins to match the holes into which they fit and for proper alignment so as to permit rotation about perpendicular axes and locking together with the wings 12 and 14 and the center universal member 16 in the same plane.

Of course, other types of locking may be used for the universal joint to lock it in place such as set screws or the like and these may accommodate locking in more than one position and thus eliminate the need for external building material that is hardenable as is currently generally used to build up the upper and lower bases in a manner to be described hereinafter. However, in the preferred embodiment, the locking pin locks the wings 12 and 14 and center disc 22 in one plane.

In FIG. 3, there is shown another embodiment of lower portion 10A of Gothic tracer having the same center universal member 16 but having different shaped right and left wings 12A and 14A. These wings are attached by holes and pins in the same manner as the embodiment of FIG. 1, but the right and left wings 12A and 14A are shaped to fit within the lingual.

The embodiment 10A is used in the same manner as the embodiment of FIG. 1 except it accommodates the mouth of persons having teeth that make it difficult to place the side wings across the ridge of the mouth because the location of the teeth interfere with such placement. In that case, the embodiment of 10A may be used by placing the lingual wings in the lingual of the mouth and having sufficient cavity for tilting of the central universal member 16.

In FIG. 4, there is a plan view of the lower portion 10 of a Gothic tracer illustrating the manner in which the right wing pin 42 and left wing pin 44 fit within holes aligned with each other in the right and left wings 12 and 14 and project into the outer ring 20 of the central universal member 16 to permit rotation about a diameter or axle formed by the pins 42 and 44. This rotation changes the angle of a central hole 26 that, as shown best in the embodiment of FIG. 1, accommodates the scribe 18 (FIG. 1).

To permit rotation about an axis perpendicular to the axis of the pins 44 and 42 and thus provide a true universal joint, posterior and anterior pins 46 and 48 similarly extend through aligned holes in the edges of the outer ring 20 and the center disc 22.

To lock the center disc 22 in the same plane as the wings 12 and 14, a locking pin 24 engages in opening 50 in one of the wings such as 14 and projects through the outer ring 20 and center disc 22 through aligned openings that lock these rings in the same plane as the wing 14. Of course, this lock may extend from any direction, and other types of locks such as set screws or a pin with a plurality of different angled openings or the like could be used for mounting the central universal member 16 in more than one position.

Figure 5:
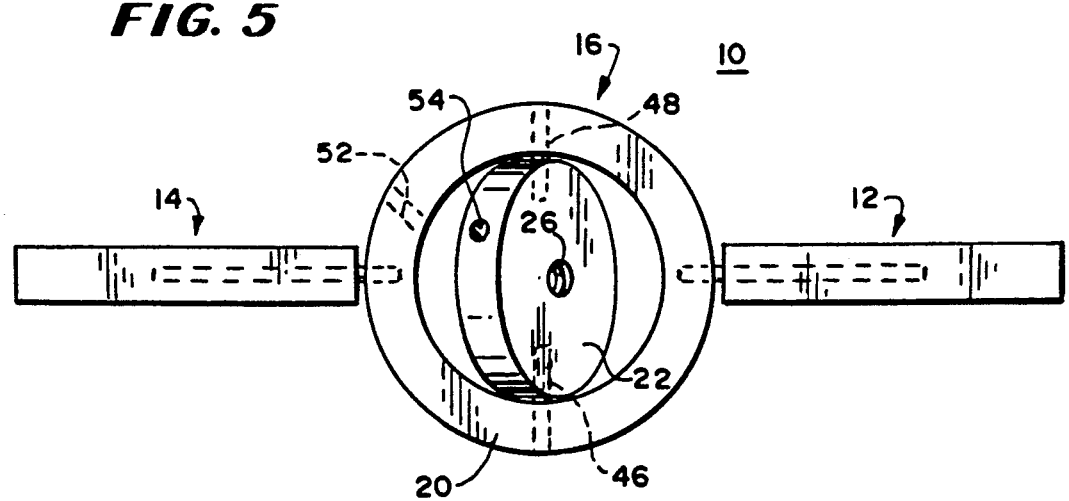
FIG. 5 is a perspective view of the lower portion of the Gothic tracer of FIG. 4 with a portion of the center disc and universal joint rotated 45 degrees from the position of FIG. 4.

In FIG. 5, there is shown a perspective view of the embodiment of FIG. 4 with the center disc 22 rotated about the posterior and anterior pins 46 and 48 by 45 degrees to expose the central tapped opening 26. Similarly, the locking pin openings 52 and 54 are shown as they would be misaligned with the pin removed so that locking does not occur. The locking pin opening 54 in the center disc 22 is offset and orthogonal to the center striking pin opening 26.

Figure 6:
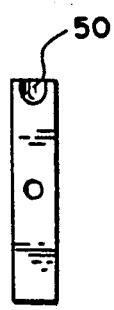
FIG. 6 is a side view of the center disc and universal joint of FIG. 4.

In FIG. 6, there is shown a side view of the wing 14 having an opening 50 for the locking pin 24 (FIG. 4) and an opening for the pin 44 in its center. As best shown in this view, the thickness of the wing is approximately 6.25 millimeters thick in the preferred embodiment and should fall in a range of between one millimeter and one centimeter.

Figure 7:
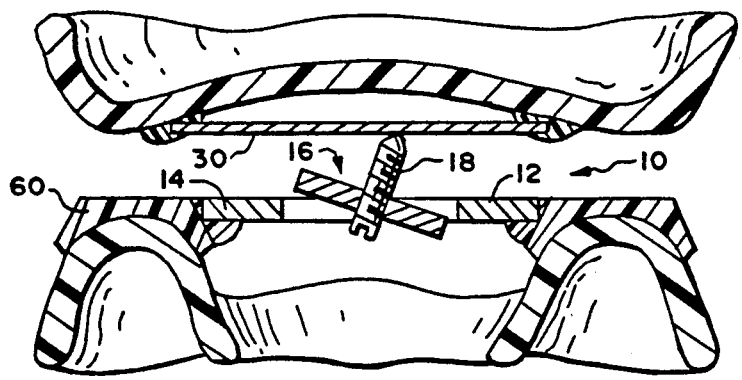
FIG. 7 is a sectional view of a portion of a mouth showing the Gothic tracer of FIGS. 1 and 2 mounted in place with the scribe articulated at an angle to the striking plate.
Figure 8:
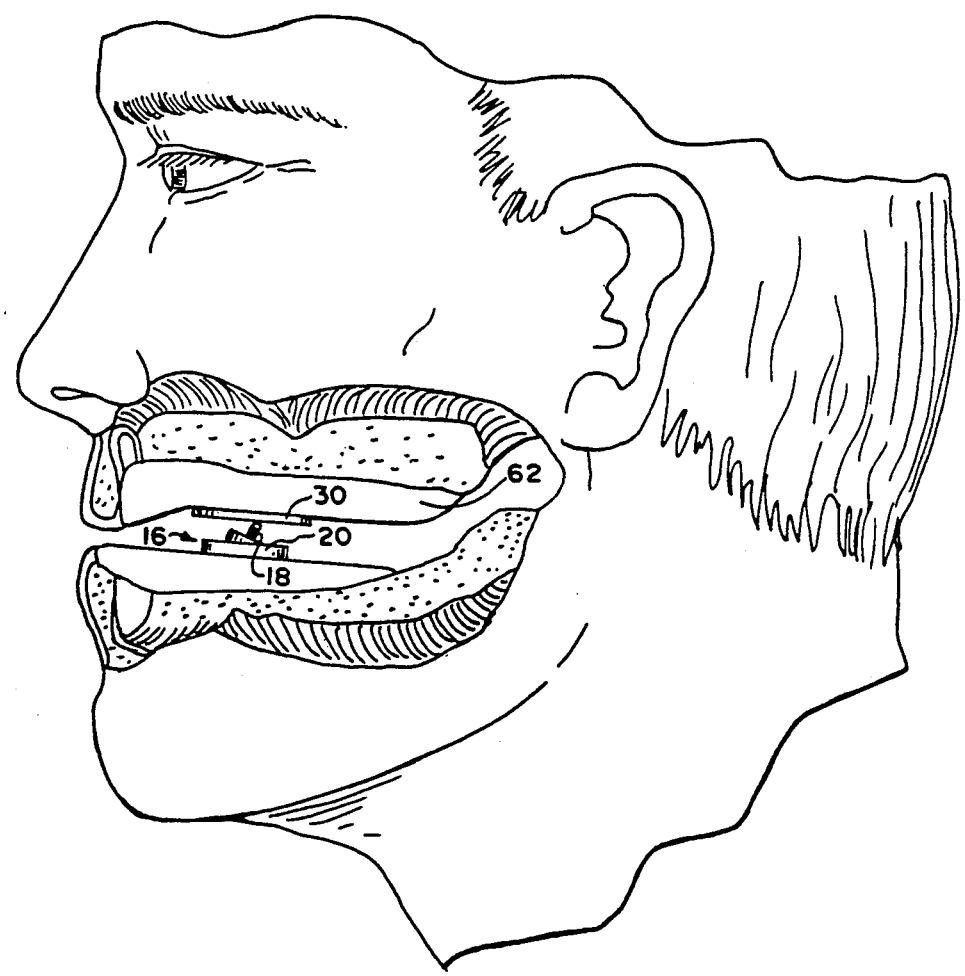
FIG. 8 is a side view of a portion of the mouth, Gothic tracer and striking plate of FIG. 7.

In FIG. 7, there is shown a sectional view of the upper and lower bases having the ridge of the teeth or bite plates 60 for the lower jaw and bite plate 62 for the upper jaw. The strike plate 30 is mounted to the upper jaw base plate 62 and the lower portion 10 of the Gothic tracer is mounted to the lower jaw base plate 60 and held in place by dental wax 16. As shown in this view, the scribe 18 is at an angle as positioned by the center disc 22 and universal joint and is in contact with the striking plate 30 with its top held in place by a stop member. In FIG. 8, there is shown a side view showing still another angle of the striking pin 18 against the striking plate 30 mounted within the embodiment 10 of Gothic tracer as it is positioned in a mouth.

In FIG. 9, there is shown a block diagram of a process 70 of forming dentures which include the step 72 of preparing a dental impression, the step 74 of preparing base plates such as 66 from the dental impression, the step 76 of determining the centric relationship, the vertical opening and the normal direction of angular motion of the jaws during articulation, the step 78 of mounting the assembly in the articulator and adjusting the articulator and the step 80 of building the denture.

The steps of preparing the dental impression 72, preparing the base plates from the dental impression 74 after the dental impressions have been removed from the mouth and the steps of mounting the assembly in the articulator and adjusting the articulator 78 and then building the denture as shown in step 80 are all conventional and routinely performed. They are not part of the invention except insofar as they cooperate with the novel apparatus of FIGS. 1–8 and the step 76 of determining the centric relationship, vertical opening and normal direction of angular motion of jaws during articulation.

There are several different approaches to step 76, but all of them involve a somewhat conventional step of adjusting the scribe to a height so that with a normally open mouth, as dentists understand that term, the tip of the pin hits the striking plate, moving the jaw so as to form centric indicia on a coating of the striking plate 30 by the scribe 18, removing the base plates that have been formed from the dental impression with the striking plate and lower portion of the Gothic tracer in place and locating the centric relationship from it.

When the centric relationship has been located, a stop member is mounted to it to accommodate the pin, with the stop member being selected in thickness to hold the tip of the pin as the jaws are permitted to relax. The plates are then unlocked and the jaw permitted to relax, which will normally move the pin to an angle with its tip in the stop member that is moved by the relaxation of the jaw. It is then locked in place with dental wax or other material and the dental bases build up into an assembly for removal from the mouth.

After the upper and lower bases are removed from the mouth, they are assembled and adjusted. The denture is then made from them. In one embodiment, the adjustments may be all made with the striking plate mounted to the upper base plate and the lower portion of the Gothic tracer to lower the base plate, the center disc and scribe being allowed to move with the jaw relaxed, the centric relationship found with the jaw relaxed, the base plate built up and removed locked in pace and then the vertical opening and centric relationship made from this one measurement. However, this approach involves calculations that the dentists are not now making and it is relatively complex. Accordingly, the preferred embodiment is shown in FIG. 10.

In FIG. 10, the step 76 includes the substep 81 of mounting the striking plate and Gothic tracer in the molded base 66, the substep 82 of returning the two base plates into the mouth with the striking plate 30 and the lower portion 10 of the Gothic tracer attached to the upper and lower base plates; the substep 84 of adjusting the scribe 18 until it touches the striking plate 30, thus determining the normal vertical opening, the substep 86 of permitting the jaws to move to mark the striking plate 30 and determine the centric relationship 38 (FIG. 2); the substep 88 of removing the top and bottom base plates again with the striking plate 30 and lower portion 10 of the Gothic tracer still in place and the substep 90 of mounting the stop member 32, adjusting it, locking it in place and building the assembly.

The stop member 32 is mounted with the opening or aperture 40 overlying the centric relationship 38 and fastened such as by dental wax or the like. This is shown in step 90 which also includes the substeps of returning the base plates to the mouth, unlocking the center disc 22 and adjusting it to a new position with the jaw relaxed. The center disc 22 is then locked in place by an epoxy or wax and the base plate is built up into an assembly which is uniform so as to show the relationships between them. They may then be removed either as one unit or, if it is necessary to break them apart, they can be removed and located back together from the marks in the wax or the like where they have been broken. The remainder of the adjustment is just as done in the prior art.

From the above description, it can be understood that the Gothic tracer and technique of this invention has several advantages, such as: (1) it permits the dentures to be originally manufactured in a manner that takes occlusion of the patient better into account; (2) it permits easy adjustment by the dentist during the making of measurements by the Gothic tracer to account for the angle of the jaw when the patient's jaws are relaxed ; (3) it permits the use of the same instrument utilized as a Gothic tracer to prepare certain types of splints or other orthodontic devices; (4) it permits the preparation of dentures with a smaller amount of chair time and irritation of the patient; and (5) it is relatively economical and easy to use.

Although a preferred embodiment of the invention has been described with particularity, many modifications and variations in the preferred embodiment may be made without deviating from the invention. Therefore, it is to be understood that, within the scope of the appended claims, the invention may be practiced other than as specifically described.

I claim:

1. A Gothic tracer comprising:
   an angularly movable member adapted to be mounted in a plurality of different angles; and
   a vertically adjustable scribe mounted to the movable member;
   said movable member is mounted by a universal joint to first and second wing members and the scribe is adjustably mounted to the movable member.

2. A Gothic tracer comprising:
   an angularly movable member adapted to be mounted in a plurality of different angles; and
   a vertically adjustable scribe mounted to the movable member;
   said movable member is mounted by a universal joint to first and second wing members and the scribe is adjustably mounted to the movable member;
   said right and left wing members are lingual wing members.

3. A Gothic tracer comprising:
   an angularly movable member adapted to be mounted in a plurality of different angles; and
   a vertically adjustable scribe mounted to the movable member;
   said movable member is mounted by a universal joint to first and second wing member sand the scribe is adjustable mounted to the movable member; p1 said right and left wing members are adapted to be mounted to the ridge of the mouth.

4. A method of making dentures comprising the steps of:
   positioning a Gothic tracer in a mouth;
   adjusting the angle of a movable member on the Gothic tracer;
   fastening the member at a fixed angle and removing it.

5. A method according to claim 4 further including the steps of:
   mounting a striking plate and lower portion of the Gothic tracer to the top and bottom base plates;
   returning the base plates into the mouth with the striking plate and Gothic tracer attached;
   adjusting a scribe in the striking plate to determine a vertical opening;
   marking the striking plate by moving the jaw to determine a centric relation;
   removing the top and bottom base plates with the striking plate and Gothic tracer attached;
   mounting a stop member of the centric relation, returning the base plates into the mouth, unlocking a center movable member and adjusting it to a new position with the jaw relaxed, locking in place to build an assembly, removing it and making a denture therefrom.

* * * * *